US010912811B1

(12) United States Patent
Stancioiu et al.

(10) Patent No.: US 10,912,811 B1
(45) Date of Patent: Feb. 9, 2021

(54) COMPOSITION FOR IMPROVING PERIPHERAL CIRCULATION AND HEALING OF HEMATOMAS

(71) Applicants: Felician Stancioiu, Bucharest (RO); Daniela Catanas, Bucharest (RO)

(72) Inventors: Felician Stancioiu, Bucharest (RO); Daniela Catanas, Bucharest (RO)

( * ) Notice: Subject to any disclaimer, the term of this patent is extended or adjusted under 35 U.S.C. 154(b) by 863 days.

(21) Appl. No.: 14/525,904

(22) Filed: Oct. 28, 2014

(51) Int. Cl.
| | |
|---|---|
| *A61K 36/00* | (2006.01) |
| *A61K 36/889* | (2006.01) |
| *A61K 9/00* | (2006.01) |
| *A61K 9/06* | (2006.01) |
| *A61K 36/185* | (2006.01) |
| *A61K 35/644* | (2015.01) |
| *A61K 36/77* | (2006.01) |
| *A61K 36/28* | (2006.01) |
| *A61K 36/11* | (2006.01) |
| *A61K 36/87* | (2006.01) |
| *A61K 36/73* | (2006.01) |
| *A61K 36/63* | (2006.01) |
| *A61K 36/537* | (2006.01) |
| *A61K 36/31* | (2006.01) |
| *A61K 36/808* | (2006.01) |
| *A61K 36/536* | (2006.01) |
| *A61K 36/752* | (2006.01) |

(52) U.S. Cl.
CPC .......... *A61K 36/889* (2013.01); *A61K 9/0014* (2013.01); *A61K 9/06* (2013.01); *A61K 35/644* (2013.01); *A61K 36/11* (2013.01); *A61K 36/185* (2013.01); *A61K 36/28* (2013.01); *A61K 36/31* (2013.01); *A61K 36/536* (2013.01); *A61K 36/537* (2013.01); *A61K 36/63* (2013.01); *A61K 36/73* (2013.01); *A61K 36/752* (2013.01); *A61K 36/77* (2013.01); *A61K 36/808* (2013.01); *A61K 36/87* (2013.01)

(58) Field of Classification Search
None
See application file for complete search history.

(56) References Cited

U.S. PATENT DOCUMENTS

| | | | | | |
|---|---|---|---|---|---|
| 3,551,554 | A | * | 12/1970 | Herschler | A61K 9/0014 424/9.4 |
| 3,711,602 | A | * | 1/1973 | Herschler | A61K 9/0014 424/45 |
| 9,107,823 | B2 | * | 8/2015 | Buyuktimkin | A61K 9/0014 |
| 2011/0217249 | A1 | * | 9/2011 | Dreher | A61K 9/0014 424/59 |
| 2011/0300083 | A1 | * | 12/2011 | Yontz | A61K 8/25 424/59 |
| 2015/0182441 | A1 | * | 7/2015 | Goutsis | A61K 8/362 132/208 |

FOREIGN PATENT DOCUMENTS

WO   WO-2012101618 A1 *   8/2012   ....... A61F 13/00063

OTHER PUBLICATIONS

Brunner et al. (2001) Br. J. Clin. Pharmacol. 51, 219-224. (Year: 2001).*
Sirtori (2001) Pharmacological Research, vol. 44, No. 3. 183-193 (Year: 2001).*
Raskin et al. (2004) Current Pharmaceutical Design 10, 3419-3429. (Year: 2004).*
Revilla et al. (1998) J. Agric. Food Chem. 46, 4592-4597. (Year: 1998).*
Website document entitled: "How to Get Rid of Spider Veins Naturally & Fast" (available at http://natural-alternative-therapies.com/how-to-get-rid-of-spider-veins) Archive to May 2013. Downloaded from website Jan. 12, 2018. (Year: 2013).*
Website document entitled: "Varicose vein attacking body butter— How to get rid of varicose veins naturally" (available at http://thecrunchymoose.com/how-to-get-rid-of-varicose-veins-naturally). Publicly posted Mar. 4, 2014. Downloaded from website Jan. 12, 2018. (Year: 2014).*
Website document entitled: "Organic Horse Chestnut Balm for Varicose Veins" (available at https://www.herbfarmacy.com/horse-chestnut-balm-20ml.html#product tabs-HF-26-30ml). Downloaded from website Jan. 12, 2018 (Year: 2018).*

* cited by examiner

*Primary Examiner* — Russell G Fiebig
(74) *Attorney, Agent, or Firm* — Michael D. Eisenberg

(57) ABSTRACT

The present invention relates to a composition for improving peripheral circulation and lymph drainage. The composition includes at least one extract of a fatty plant, at least one extract of a plant having astringent properties, and at least one extract of a plant with one or more effects including anti-inflammatory, formation of new, healthy collagen fibrilles, antiseptic properties, antioxidant, neutralizing free radicals, antiedematous, vitaminazing, and stimulating wound healing. The composition may be used to treat at least one of varicose veins, swollen legs, painful legs, stasis dermatitis, swollen arms, indurated arms, hematomas, ecchymosis, periorbital dark circles, periorbital swelling, and hemorrhoids.

11 Claims, No Drawings

COMPOSITION FOR IMPROVING PERIPHERAL CIRCULATION AND HEALING OF HEMATOMAS

TECHNICAL FIELD

The present invention, in some embodiments thereof, relates to health and natural products. Specifically it relates to products to improve poor circulation or lymph drainage and healing of hematomas.

BACKGROUND OF THE INVENTION

The circulatory system, composed of the lymphatic and cardiovascular systems, is an essential system in the human body. The cardiovascular system is a closed system which specifically allows for transport of nutrients, oxygen, and hormones and helps to regulate homeostasis in the body, pH, and body temperature. The lymphatic system is an open system and one of its main functions is to provide an accessory route for the excess liters of plasma that is processed through capillary filtration, so as to return the excess liters of plasma back into blood. Another function of the lymphatic system is the defense in the immune system. In fact, lymph is very similar to blood plasma in composition but contains no red cells and has modified white blood cells, which are important elements in the immune system.

Proper functioning of these systems is crucial to maintain a healthy body. Poor circulation, for example, can have consequences ranging from aesthetic (tortuous veins) to health consequences including: discomfort, pain, inflammation, formation and propagation of thrombi, and stasis ulcers. Poor drainage in the lymphatic system can also lead to swelling, induration, and skin breakage. While poor drainage may occur due to parasites or conditions, such as elephantiasis, it can also result from other medicinal treatments. Chemotherapy administration, for example, after mastectomy is usually performed on one arm only. In some patients persistent ecchymosis, due to frail veins, swelling and fibrous organization of tissue, can be a lasting problem. Also in some oncological patients radiotherapy impairs the lymph drainage and results in severely swollen, painful limbs which require many hours of massage therapy.

Impaired circulation in lower limbs can usually be attributed to problems in the wall of the veins (saphenous veins) of the legs (trauma, inflammation, etc.), the lack of facilitatory movements of the legs which normally are helping venous and lymphatic return and valves inside the veins which are not closing well, allowing blood stasis in such veins and distension of the vein wall.

Poorly oxygenated blood in such areas further gives rise to local modifications of the pH of the blood, shift of the metabolic process in the anaerobic mode, with the ensuing decrease in efficacy of the energy generating processes of metabolic reactions in cells' mitochondria, an increased amount of free, unbuffered radicals (O— and OH—) and the consequent changes in the microenvironment represented by the endothelial wall, valves, and poor quality blood.

Currently these problems are approached from a number of different directions. Some ointments use heparin, an anticoagulant that can prevent clots, to lower blood viscosity and obstruct formation of thrombi. Heparin, however, may cause heparin-induced thrombocytopenia. This is caused by an immunological reaction that immunological response to target platelets. Heparin has also been associated with an elevation in levels of aminotransferase and the concentration of the electrolyte potassium ($K^+$). Other ointments may contain plant extracts from sources such as: wild chestnut (*Aesculus hippocastanum*), grapevine leaves (*Vitis vinifera*), and *Centella asiatica* or gotu-kola. The current treatments using plants extracts are designed to produce primarily an astringent effect but do not have antioxidant, anti-inflammatory, antiseptic and regenerative properties. Surgery, both traditional and laser, have been used to remove varicose veins. Chemicals may be injected into the tortuous veins, such as: sodium morrhuate, potassium alum, and eicosapentaenoic acid. Exertion of mechanical pressure through devices such as elastic socks may help reduce risk of thrombi formation in situations of extended inactivity.

BRIEF SUMMARY OF EMBODIMENTS OF THE INVENTION

The complications associated with the related conditions of poor circulation, poor oxygenation, inflammation and problems in vein walls described above are complex. Because of the relationship between these complications and the differing procedures of treatment, often several types of treatments may be needed. Current treatments may be surgical, require a patient to wear a specified garment, or involve time consuming physical therapy for massages. Current treatments involving other topical solutions may make use of non-natural sources or require care in selecting from a multitude of sources to address the complex set of problems. Selecting from a variety of potential treatments requires careful consideration of potential conflicts and synergistic effects. Current ointments use a combination of 2-3 plant extracts which are known for their astringent action on the vein wall. These ointments specifically use extracts of horse chestnut, vine leaves, bilberry, and gotu kola. However, many aspects of the related problems remain unaddressed such as: the improvement in the properties of the vein wall and some inflammatory and metabolic processes. The current ointments have an astringent effect rather than antioxidant, anti-inflammatory, antiseptic and regenerative properties.

There is therefore a need for an ointment containing natural ingredients that can be applied directly to the skin. Such an ointment would help the individual to avoid surgery, wearing of unwieldy physical devices, and time consuming procedures. It would also allow a patient to have access to a unique assortment of ingredients which work together synergistically against a complex and related set of problems. A successful treatment requires more than one class of substances that can address concomitantly many of the modifications (e.g. changes of the vascular endothelium, local pH, oxygen levels, paracrine and cytokine molecules) brought about by the poor venous and/or lymph return. As non-limiting examples, embodiments of the proposed composition can address circulatory problems of the lower limbs (varicose veins, heavy legs, swollen legs, painful legs, hyperpigmentation of the skin following blood stagnation, calf and ankle edema, and lymphatic circulation blockage); dark circles and swollen areas under the eyes (suborbital hyperpigmentation and edema); post-chemotherapy and radiotherapy in a limb that is swollen, indurated (hardened) with bruises and frail veins; healing (resorption) of hematomas, or in hemorrhoidal disease.

The present invention in some embodiments thereof, invention relates to health and natural products. Specifically it relates to products to improve poor circulation or lymph drainage.

In some embodiments of the present invention, a composition is provided that includes many plant extracts, described further below, in concentrations that act synergistically to improve the flow of blood in veins and in lymph vessels via different yet complementary mechanisms. A preparation method of the present invention increases the extraction and activity of the components.

An aspect of some embodiments of the present of the present invention relates to a composition for improving peripheral circulation and lymph drainage. The composition includes:

at least one plant extract from a first group comprising the following fatty plant extracts: palm oil, palm kernel oil (*Elaeis guineensis*), coconut oil (*Cocos nucifera*), cocoa butter (*Theobroma cacao*), shea butter (*Vitellaria paradoxa*), beeswax;

at least one plant extract from a second group comprising plant extracts from the following plants: horse chestnut (*Aesculus hippocastanum*), horseweed (*Conyza canadensis*), horsetail (*Equisetum arvense*), common witch-hazel (*Hamamelis virginiana*), hazelnut leaves (*Corylus avellana*), vine leaves (*Vitis vinifera*), meadowsweet (*Filipendula ulmaria*), ash tree leaves (*Frasinus excelsior*), *Salvia sclarea*, *Verbascum thapsus*, *Lythrum salicaria*, *Hypericum perforatum*, *Capsella bursa pastoris*, *Polygonum aviculare*, *Agrimonia eupatoria*, *Lamium purpureum*, *Rubus idaeus*, *Alangium salviflorum*, *Polygonum hydropiper*, *Achilea millefolium*, *Quercus robur*, gotu-kola (*Centella asiatica*). *Verbascum thapsus*, *Galium aparine*, *Linaria officinalis*, *Borago officinalis*, *Melissa oficinalis*, and *Galium verum*;

at least one plant extract from a second group comprising plant extracts from the following plants: hornbeam (*Carpinus betulus*), greater burdock (*Arctium lappa*), watercress (*Nasturtium officinale*), figwort (*Scrophularia nodosa*), hedge mustard (*Sisymbrium officinale*), costmary (*Tanacetum balsamita*), danewort (*Sambucus ebulus*), common self-heal (*Prunella vulgaris*), fava bean leaves (*Vicia faba*), common bean sheaths (*Phaseolus vulgaris*), common daisy (*Bellis perennis*), squash (*Cucurbita pepo*), three-lobe beggarticks (*Bidens tripartita*), common groundsel (*Senecio vulgaris*), lavender (*Lavandula angustifolia*), brooklime (*Veronica beccabunga*), bastard balm (*Melittis melissophyllum*), bittercress (*Barbarea vulgaris*), martagon (*Lilium martagon*), birthwort (*Aristolochia clematis*), northern fir moss (*Huperzia selago*), common beech (*Fagus sylvatica*), sorrel (*Rumex acetosa*), dog-rose (*Rosa canina*), wall germander (*Teucrium chamaedrys*), dyer's broom (*Genista tinctoria*), celandine (*Chelidonium majus*), old man's beard (*Clematis vitalba*), alpine anemone (*Pulsatilla* montana), bay laurel (*Laurus nobilis*), pepper (*Capsicum annuum*), turmeric (*Curcuma longa*), ragged robin (*Lychnis flos-cuculi*), elder (*Sambucus nigra*), tea tree oil (*Melaleuca alternifolia*), comfrey (*Symphytum officinale*), ankotha (*Alangium salviflorum*), yellow bedstraw (*Galium verum*), daisy leaves (*Leucanthemum vulgare*), basil (*Ocimum basilicum*), potato (*Solanum tuberosum*), lemon oil (*Citrus limon*), birch (*Betula pendula*), lingonberry (*Vaccinium vitis-idaea*), grapefruit seed oil (*Citrus paradisi*), wheat (*Triticum* spp), rice (*Oryza* spp), and neem.

In a variant, the first group further comprises fatty plant extracts which comprise hydrogenated plant fat.

Optionally, the first group comprises at least one of soy wax and hydrogenated soy oil.

In another variant, the at least one plant extract from the first group forms about 0.1% to about 70% of the composition's weight. Each of all other plant extracts has a concentration between about 0.1% to about 10%/of the composition's weight.

In yet another variant, the composition further comprises at least one component from a fourth group of components comprising at least one of dimethyl sulfoxide and allantoin.

Optionally, the at least one component from the fourth group forms about 0.1% to about 30% of the composition's weight.

In a further variant, the composition is configured into a solid bar configured for being rubbed on skin.

In yet a further variant, the composition is liquid and is in a form of at least one of: an ointment, a cream, an emulsion, a lotion, a suspension, and a gel.

Optionally, the composition is configured as a fluid emulsion configured for being pumped through a pumping mechanism.

Another aspect of some embodiments of the present invention relates to a method for improving one of peripheral circulation, lymph drainage, and treating at least one of varicose veins, swollen legs, painful legs, stasis dermatitis, swollen arms, indurated arms, hematomas, ecchymosis, periorbital dark circles, periorbital swelling, and hemorrhoids, the method comprising applying the above described composition to bare skin.

A further aspect of some embodiments of the present invention relates to a composition for improving peripheral circulation and lymph drainage. The composition comprises:

at least one component from a first group comprising at least one of: animal fat, palm oil, palm kernel oil (*Elaeis guineensis*), coconut oil (*Cocos nucifera*), cocoa butter (*Theobroma cacao*), shea butter (*Vitellaria paradoxa*), beeswax, hydrogenated plant fat extract;

at least one plant extract from a second group comprising plant extracts from the following plants: horse chestnut (*Aesculus hippocastanum*), horseweed (*Conyza canadensis*), horsetail (*Equisetum arvense*), common witch-hazel (*Hamamelis virginiana*), hazelnut leaves (*Corylus avellana*), vine leaves (*Vitis vinifera*), meadowsweet (*Filipendula ulmaria*), ash tree leaves (*Frasinus excelsior*), *Salvia sclarea*, *Verbascum thapsus*, *Lythrum salicaria*, *Hypericum perforatum*, *Capsella bursa pastoris*, *Polygonum aviculare*, *Agrimonia eupatoria*, *Lamium purpureum*, *Rubus idaeus*, *Alangium salviflorum*, *Polygonum hydropiper*, *Achilea millefolium*, *Quercus robur*, gotu-kola (*Centella asiatica*). *Verbascum thapsus*, *Galium aparine*, *Linaria officinalis*, *Borago officinalis*, *Melissa oficinalis*, and *Galium verum*;

at least one plant extract from a second group comprising plant extracts from the following plants: hornbeam (*Carpinus betulus*), greater burdock (*Arctium lappa*), watercress (*Nasturtium officinale*), figwort (*Scrophularia nodosa*), hedge mustard (*Sisymbrium officinale*), costmary (*Tanacetum balsamita*), danewort (*Sambucus ebulus*), common self-heal (*Prunella vulgaris*), fava bean leaves (*Vicia faba*), common bean sheaths (*Phaseolus vulgaris*), common daisy (*Bellis perennis*), squash (*Cucurbita pepo*), three-lobe beggarticks (*Bidens tripartita*), common groundsel (*Senecio vulgaris*), lavender (*Lavandula angustifolia*), brooklime (*Veronica beccabunga*), bastard balm (*Melittis melissophyllum*), bittercress (*Barbarea vulgaris*), martagon (*Lilium martagon*), birthwort (*Aristolochia clematis*), northern fir moss (*Huperzia selago*), common beech (*Fagus sylvatica*), sorrel (*Rumex acetosa*), dog-rose (*Rosa canina*), wall germander (*Teucrium chamaedrys*), dyer's broom (*Genista tinctoria*), celandine (*Chelidonium majus*), old man's beard (*Clematis vitalba*), alpine anemone (*Pulsatilla* montana), bay laurel (*Laurus nobilis*), pepper (*Capsicum annuum*), turmeric (*Curcuma longa*), ragged robin (*Lychnis flos-cuculi*), elder (*Sambucus nigra*), tea tree oil (*Melaleuca alternifolia*), comfrey (*Symphytum officinale*), ankotha (*Alangium salviflorum), yellow bedstraw (*Galium verum*), daisy leaves (*Leucanthemum vulgare*), basil (*Ocimum basilicum*), potato (*Solanum tuberosum*), lemon oil (*Citrus limon*), birch (*Betula pendula*), lingonberry (*Vaccinium vitis-idaea*), grapefruit seed oil (*Citrus paradisi*), wheat (*Triticum* spp), rice (*Oryza* spp), and neem.

Yet another aspect of some embodiments of the present invention relaters to a method for creating a composition that improves peripheral circulation and lymph drainage. The method comprises:

Step 1: mixing plant extracts to create a mixture, the plant extracts comprising:

at least one plant extract from a first group comprising the following fatty plant extracts: palm oil, palm kernel oil (*Elaeis guineensis*), coconut oil (*Cocos nucifera*), cocoa butter (*Theobroma cacao*), shea butter (*Vitellaria paradoxa*), beeswax, and hydrogenated plant fat extract;

at least one plant extract from a second group comprising the following plant extacts: horse chestnut (*Aesculus hippocastanum*), horseweed (*Conyza canadensis*), horsetail (*Equisetium arvense*), common witch-hazel (*Hamamelis virginiana*), hazelnut leaves (*Corylus avellana*), vine leaves (*Vitis vinifera*), meadowsweet (*Filipendula ulmaria*), ash tree leaves (*Frasinus excelsior*), *Salvia sclarea*, *Verbascum thapsus*, *Lythrum salicaria*, *Hypericum perforatum*, *Capsella bursa pastoris*, *Polygonum aviculare*, *Agrimonia eupatoria*, *Lamium purpureum*, *Rubus idaeus*, *Alangium salviflorum*, *Polygonum hydropiper*, *Achilea millefolium*, *Quercus robur*, gotu-kola (*Centella asiatica*). *Verbascum thapsus*, *Galium aparine*, *Linaria officinalis*, *Borago officinalis*, *Melissa oficinalis*, and *Galium verum*;

at least one plant extract from a second group comprising plant extracts from the following plants: hornbeam (*Carpinus betulus*), greater burdock (*Arctium lappa*), watercress (*Nasturtium officinale*), figwort (*Scrophularia nodosa*), hedge mustard (*Sisymbrium officinale*), costmary (*Tanacetum balsamita*), danewort (*Sambucus ebulus*), common self-heal (*Prunella vulgaris*), fava bean leaves (*Vicia faba*), common bean sheaths (*Phaseolus vulgaris*), common daisy (*Bellis perennis*), squash (*Cucurbita pepo*), three-lobe beggarticks (*Bidens tripartita*), common groundsel (*Senecio vulgaris*), lavender (*Lavandula angustifolia*), brooklime (*Veronica beccabunga*), bastard balm (*Melittis melissophyllum*), bittercress (*Barbarea vulgaris*), martagon (*Lilium martagon*), birthwort (*Aristolochia clematis*), northern fir moss (*Huperzia selago*), common beech (*Fagus sylvatica*), sorrel (*Rumex acetosa*), dog-rose (*Rosa canina*), wall germander (*Teucrium chamaedrys*), dyer's broom (*Genista tinctoria*), celandine (*Chelidonium majus*), old man's beard (*Clematis vitalba*), alpine anemone (*Pulsatilla* montana), bay laurel (*Laurus nobilis*), pepper (*Capsicum annuum*), turmeric (*Curcuma longa*), ragged robin (*Lychnis flos-cuculi*), elder (*Sambucus nigra*), tea tree oil (*Melaleuca alternifolia*), comfrey (*Symphytum officinale*), ankotha (*Alangium salviflorum*), yellow bedstraw (*Galium verum*), daisy leaves (*Leucanthemum vulgare*), basil (*Ocimum basilicum*), potato (*Solanum tuberosum*), lemon oil (*Citrus limon*), birch (*Betula pendula*), lingonberry (*Vaccinium vitis-idaea*), grapefruit seed oil (*Citrus paradisi*), wheat (*Triticum* spp), rice (*Oryza* spp), and neem;

Step 2: warming the mixture to about 80-100° C. while mixing;

Step 3: adding water to the mixture while continuously mixing the mixture at about 80-100° C. for a period of up to 60 minutes to produce an emulsion, the water forming up to 10% of a final weight of the emulsion;

Step 4: leaving the emulsion to cool and macerate for between 1 and 12 hours;

Step 5: sifting the emulsion to remove plant detritus; and

Step 6: leaving the emulsion to congeal at or below.

In a variant, the mixing further comprises mixing a dimethyl sulfoxide and/or allantoin with the plant extracts.

In another variant, the hydrogenated plant fat extract comprises soy wax and hydrogenated soy oil.

In yet another variant, the method comprises adding one or more additional plant extracts prior to the congealing of the emulsion, the one or more additional plant extracts belonging to one or more of the first group, the second group, and the third group.

In a further variant, the plants may be whole, in parts, in powder form, fresh, or dry.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

An aspect of some embodiments of the present invention relates to health and natural products. Specifically it relates to products to improve poor circulation or lymph drainage.

The present invention relates to a composition that uses a synergistic approach of treating malfunction in peripheral blood and/or lymph circulation with many related features as well as a unique process for producing that composition.

Each constituent plant extract, described below, contains different active ingredients in different quantities. These active ingredients contained in the constituent extracts act on both physiologic and pathologic pathways. Biochemical pathways are regulated by key cofactors and enzymes. The relevant pathways in treating poor circulation or lymph drainage contain redundancies. Treatment that blocks only one pathway may be overcome by increased compensatory behavior in another pathway regulated by different cofactors or enzymes.

Inflammation, a process which occurs in infections, injury, some tumor growth, is a process mediated by hundreds of molecules present in the body. Therefore many different pathways are to be affected. The specific plurality of different active ingredients present in the constituents of the present invention has the following effects: anti-inflammatory, formation of new, healthy collagen fibrilles, antiseptic properties, antioxidant, neutralizing free radicals, antiedematous, vitaminizing, and stimulation of wound healing. This specific variety of effects acts in a synergistic approach to improve the physiological functions of the veins and lymph vessels. Without the synergistic effect, an individual treatment from one type of extract would likely either be ineffective or less effective. As will be explained below, effective results have been achieved using some variants of the composition of the present invention. The following description of the constituent plant extracts in the embodiments of the composition have biochemical evidence of producing astringent effects, anti-inflammatory effects, antioxidants, buffering of free oxidizing radicals, and improving the local oxygen content and pH.

The composition of the present invention includes constituents from three groups. At least one constituent from each group is present in the composition. In some embodiments of the present invention, more than one constituent from any one of the three groups is present. The groups include: a first group, which includes fatty plant extracts which make up the base of the ointment (up to about 70% in weight); a second group, which includes extracts from plants with known astringent properties, or that stimulate lymph circulation; and a third group, which includes plant extracts with varying effects including anti-inflammatory, formation of new, healthy collagen fibrilles, antiseptic properties, antioxidant, neutralizing free radicals, antiedematous, vitaminazing, and stimulating wound healing.

According to some embodiments of the present invention, the plant extracts used in the compositions have respective concentrations ranging from approximately 0.1% to approximately 10% by weight. The fatty plant extracts of the first group form the base of the composition, and form up to about 70% of the ointment's weight.

The fatty plant extracts of the first group are composed primarily of esterified fatty acids, both unsaturated and saturated, which are important components of any cellular membrane. These specific extracts are nourishing for skin (epidermis). Additionally they have known emollient and humectant action on the epidermis, which decreases inflammation and the production of pro-inflammatory molecules locally (eicosanoides, arachidonic acid) and inhibit the production of cytokines and chemoattractants for the cellular effectors of inflammation (macrofages, lymphocytes, etc.). All these plants have in their composition various amounts of glycerin esters of unsaturated fatty acids oleate (monounsaturated), linoleate (polyunsaturated), and alpha-linolenate (polyunsaturated) furthermore some ingredients of shea butter (triterpene cinnamates and acetates) were shown to exert direct anti-inflammatory actions. The fatty plant extracts used as the base for the mixture can be any fatty plant extract, may include an extract from single plant type, or a combination of extracts from different plant types. The following plant types may be used, for example, and have been successfully used by the inventor: palm oil, palm kernel oil, coconut oil, cocoa butter, shea butter, and beeswax. These extracts can be used interchangeably. Fatty acids with more stearic acid esters (which are solid at room temperature), help to create a more solid base. Fatty extracts of any plant can be used as a base for the mixture. If the fatty extract used is fluid at room temperature, the composition can be made to assume a fluid form, so that the composition can be dispensed from a vial with a pump.

Optionally, fatty extracts having hydrogenated plant fats are included in the first group (soy wax and/or hydrogenated soy oil, for example) but such extracts do have some pro-inflammatory actions that may be deleterious to blood vessels and tissues in general. In some embodiments the first group may include fats from animal sources, which may be used alone or in addition to one or more fatty plant extracts.

The plant extracts of the second group are intended for astringent purposes. These extracts include extracts from horse chestnut (*Aesculus hippocastanum*), horseweed (*Conyza canadensis*), horsetail (*Equisetum arvense*), common witch-hazel (*Hamamelis virginiana*), hazelnut leaves (*Corylus avellana*), vine leaves (*Vitis vinifera*), meadowsweet (*Filipendula ulmaria*), ash tree leaves (*Frasinus excelsior*), *Salvia sclarea*, *Verbascum thapsus*, *Lythrum salicaria*, *Hypericum perforatum*, *Capsella bursa pastoris*, *Polygonum aviculare*, *Agrimonia eupatoria*, *Lamium purpureum*, *Rubus idaeus*, *Alangium salviflorum*, *Polygonum hydropiper*, *Achilea millefolium*, *Quercus robur*, gotu-kola (*Centella asiatica*). *Verbascum thapsus*, *Galium aparine*, *Linaria officinalis*, *Borago officinalis*, *Melissa oficinalis*, and *Galium verum*. These extracts are known from their traditional use in some European countries, to stimulate lymph circulation.

The plant extracts of the third group are plant extracts that exert their effects on related biological systems and therefore have a multitude of know activities including: anti-inflammatory, formation of new and healthy collagen fibrilles, antiseptic properties, antioxidant, neutralizing free radicals, antiedematous, vitaminizing, and some stimulate wound healing. All act in a synergistic fashion towards improving the physiological function of the veins and lymph vessels. These plant extracts include: hornbeam (*Carpinus betulus*), greater burdock (*Arctium lappa*), watercress (*Nasturtium officinale*), figwort (*Scrophularia nodosa*), hedge mustard (*Sisymbrium officinale*), costmary (*Tanacetum balsamita*), danewort (*Sambucus ebulus*), common self-heal (*Prunella vulgaris*), fava bean leaves (*Vicia faba*), common bean sheaths (*Phaseolus vulgaris*), common daisy (*Bellis perennis*), squash (*Cucurbita pepo*), three-lobe beggarticks (*Bidens tripartita*), common groundsel (*Senecio vulgaris*), lavender (*Lavandula angustifolia*), brooklime (*Veronica beccabunga*), bastard balm (*Melittis melissophyllum*), bittercress (*Barbarea vulgaris*), martagon (*Lilium martagon*), birthwort (*Aristolochia clematis*), northern fir moss (*Huperzia selago*), common beech (*Fagus sylvatica*), sorrel (*Rumex acetosa*), dog-rose (*Rosa canina*), wall germander (*Teucrium chamaedrys*), dyer's broom (*Genista tinctoria*), celandine (*Chelidonium majus*), old man's beard (*Clematis vitalba*), alpine anemone (*Pulsatilla* montana), bay laurel (*Laurus nobilis*), pepper (*Capsicum annuum*), turmeric (*Curcuma longa*), ragged robin (*Lychnis flos-cuculi*), elder (*Sambucus nigra*), tea tree oil (*Melaleuca alternifolia*), comfrey (*Symphytum officinale*), ankotha (*Alangium salviflorum*), yellow bedstraw (*Galium verum*), daisy leaves (*Leucanthemum vulgare*), basil (*Ocimum basilicum*), potato (*Solanum tuberosum*), lemon oil (*Citrus limon*), birch (*Betula pendula*), lingonberry (*Vaccinium vitis-idaea*), grapefruit seed oil (*Citrus paradisi*), wheat (*Triticum* spp), rice (*Oryza* spp), and Neem.

In some embodiments of the present invention, the composition also includes allantoin and/or dimethyl sulfoxide (DMSO), which are organic man-made compounds configured to further improve the properties of the composition. Both act towards improving the physical properties of the composition by helping homogenize the composition's lipid and aqueous phase, conserving its ingredients and furthermore by exerting direct biological actions as very potent antioxidants. In one embodiment of the present invention, only allantoin is present and forms up to 30% of the composition's weight. In another embodiment of the present invention, only DMSO is present and forms up to 30% of the composition's weight. In yet another embodiment of the present invention, allantoin and DMSO are present and together form up to 30% of the composition's weight.

Different variations of the composition of the present invention have already been used successfully by patients in a clinical study which began in April 2014, for the purpose of evaluating the efficacy of the composition of the present invention and possible safety problems. Two medical doctors used the composition of the present invention on patients and evaluated the results after its use within an open-label, consecutive-patient study. Between Apr. and Jul. 31, 2014 more than 22 such patients were treated with the composition of the present invention with excellent results. There were improvements that were not obtained with other treatments. There were no allergic reactions reported, and in all but one patient there was noticeable improvement in the discomfort, pain alleviation, reduction of swelling, induration, normalization of color of skin and less protuberant veins. Many of those patients have previously used other products, both pharmaceutical and natural extracts. The efficacy of the ointment was shown by treating more than 20 consecutive patients and resulting in improved condition in more than 90% of the patients. The probability that this ointment is beneficial for the patients is statistically significant ($p<0.05$).

Examples of the variations of the compositions of the present invention that are especially beneficial for specific purposes are listed below.

For treating varicose veins, swollen, painful legs, and stasis dermatitis, the following variant of the composition of the present invention may be used: from the first group, one or more fatty plant extracts; DMSO and/or allantoin; from the second group, horse chestnut, *Betula pendula*, and *Vitis vinifera*; from the third group, *Solanum tuberosum*, Lemon balm, and lemon oil.

For treating swollen, indurated arms the following variant of the composition of the present invention may be used: from the first group, one or more fatty plant extracts; DMSO and/or allantoin; from the second group, *Prunella vulgaris*, horse chestnut; from the third group, *Conyza Canadensis, Equisetium arvense, Triticum* spp, grapefruit seed oil, and lemon oil.

For treating hematomas and ecchymosis, the following variant of the composition of the present invention may be used: from the first group, one or more fatty plant extracts; DMSO and/or allantoin; from the second group, Hazelnut leaves, *Vitis vinifera*; from the third group: *Frasinus excelsior, Oryza sativa*, Lemon oil.

For treating periorbital dark circles and swelling the following variant of the composition of the present invention may be used: from the first group, one or more fatty plant extracts; DMSO and/or allantoin; from the second group, *Centella asiatica, Galium verum*; from the third group, *Rosa canina, Triticum* spp, and lemon oil.

For treating hemorrhoids the following variant of the composition of the present invention may be used: from the first group, one or more fatty plant extracts; DMSO and/or allantoin; from the second group *Hammamelis virginiana* and *Vitis vinifera*; from the third group, *Solanum tuberosum*, Tea tree oil, grapefruit seed oil.

An aspect of some embodiments of the present invention relates to a method or preparation of the present invention. The method is designed to increase extraction and efficacy of the components. In particular a lipid phase extraction is used in conjunction with an aqueous phase extraction. The preparation method involves though the following steps:

1. At least one plant extract from the first group, is mixed together with at least one plant or plant extract from a plant of the second group and with at least one plant or plant extract from a plant of the third group described above. The mixing may be performed manually or with the help of mechanical/electrical mixer The specific plant extracts are selected according to a specific need, such as nourishing the skin or for astringent purposes. Some plants are used in a dried or powdered form and others in fresh condition. In one embodiment most or all plants are freshly picked. In some cases dried plants produce effective results in the extraction of the desired extracts and may be a necessity depending on the season of preparation and availability of the plants themselves. Some plants are used whole while for some just specific parts are used. In one embodiment leaves are used from the plants of the second and third groups, while an extract is used from the first group.

2. The mixture of fat and plant extracts is placed in a water bath and warmed to about 80-100° C. while being continuously mixed. When all of the fat is melted and the mixture is in liquid form, purified water is added measuring up to 10% the final weight. The resulting mixture is kept in the water bath and is continuously mixed for better homogenization for a period of up to 60 minutes, to form an emulsion. The resulting emulsion containing fat, water, and plant extracts is then left at 80-100° C. for 1-30 minutes depending on the composition. The length of time depends on which form of extract and individual plant was elected to use in the ointment. Dried plants may require up to 30 minutes; fresh plants require less time for extraction. The powdered form requires the least 1-3 minutes for extraction.

3. The emulsion is left to cool and macerate for anywhere between 1 and 12 hours.

4. The emulsion is then sifted. The remaining mixture of plants in the emulsion is pressed (or squeezed) to obtain a fluid containing the active ingredients from the plant.

5. The emulsion is left to congeal either at room temperature or in the refrigerator, and then poured in vials.

Optionally, after the sifting and before the congealing, additional plants or plant extracts belonging to one or more of the first, second, and third group, are added to the emulsion. In some embodiments of the present invention, at least one plant associated with the third group is added between the sifting and the congealing. In one embodiment the additional plant extracts added include neem, gotu kola, wild chestnut, and potato. Generally, any extracts from plants of the third group may be used interchangeably at this step. In another embodiment the additional plants or plants extracts include plants or extracts of plants belonging to the second group (astringent, and beneficial for lymph circulation), and plants or extracts of plants belonging to the third group (synergistic).

The differentiation that occurs at the optional step between the sifting and the congealing allows the ointment to be focused or strengthened in order to be effective for a chosen treatment. The treatments may include: a. treatment of varicose veins; b. treatment periorbital dark circles, and resorption (accelerating healing) of hematomas; c. Chemo- and radio-therapy adjuvants (used in palliative care); d. treatment of hemorrhoidal disease. Plants and plant extracts that are added at the optional step between the sifting and the congealing may or may not include repeats of plants or extracts that were added at an earlier stage. For example, the addition of potato in step 4 does not preclude the use of potato in step 1. The use of plants and plant extracts in step 1 creates a functional base for the composition. The types or amounts of the additional extracts depend on the preference of the user regarding features that the user wishes to enhance in the composition as described above.

Storage depends on the chosen composition of plant extracts. Solid fats in the composition melt at different temperatures ranging from around 25° C. to about 50° C. Because some solid fats are optionally included in the different variations of the composition of the present invention, the melting point may change in an individual embodiment. Generally an ointment formed by the composition of the present invention can be stored at about 25° C. while avoiding direct sunlight on the vial (as temperature within the vial can reach 40 or 50° C., at which point the ointment will liquefy) or can be stored in the refrigerator.

The composition of the present invention, in a non-limiting example, is in the form of an ointment. The ointment is configured for being applied to clean skin in areas of the skin that show signs of malfunctions in peripheral blood and/or lymph circulation and is rubbed into the skin with a gentle massaging action. A user may select the amount to use, but a typical use may be about 1-3 g.

In further non-limiting examples the form may differ. The form of the composition in other embodiments may be solid and used as a bar. The composition may also be fluid such as a cream, emulsion, or gel. Changes in the viscosity of the composition may relate to which fatty plant extracts are used and which form a user prefers. These changes would enable different functional packaging including allowing the invention to either be pumped through a mechanical pumping action or being scooped out by hand.

Uses of the composition of the present invention mentioned above have included treatment of varicose veins, swollen arm and forearm due to chemo- or radiotherapy administration, lymphedema, and postural edema of lower legs, periorbital dark circles, hematomas, and hemorrhoids. The composition of the present invention, however, may be used for more purposes, such as treatment of swollen ankles/lower limbs associated with conditions such as cardiac insufficiency, renal disease, filariasis, obstruction of venous/lymphatic return.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A composition for improving peripheral circulation and lymph drainage, the composition comprising:
   (a) an effective amount at least one fat serving a base of the composition, selected from a first group consisting of the following fats: palm oil, palm kernel oil (*Elaeis guineensis*), coconut oil (*Cocos nucifera*), cocoa butter (*Theobroma cacao*), shea butter (*Vitellaria paradoxa*), beeswax, and hydrogenated plant fat;
   (b) an effective amount of a first plant extract with astringent properties selected from a group of plant extracts consisting of: horse chestnut (*Aesculus hippocastanum*), vine leaves (*Vitis vinifera*), gotu-kola (*Centella asiatica*), *Capsella bursa pastoris* and *Linaria officinalis;*
   (c) an effective amount of a second plant extract having a known desired effect on a biological system selected from the group consisting of: potato (*Solanum tuberosum*), lemon (*Citrus limon*), birch (*Betula pendula*), grapefruit seed (*Citrus paradisi*), and rice (*Oryza* spp);
   (d) an effective amount of dimethyl sulfoxide (DMSO) forming up to 30% of the composition's weight and being present in at least a minimal amount required for the DMSO to exert direct biological actions as an antioxidant;
wherein the first and second plant extracts are extracted by maceration in the at least one fat, the maceration comprising: the maceration comprising:
   mixing plant parts with the at least one fat to generate a mixture;
   warming the mixture to about 80 to 100° C. while mixing;
   adding water to the mixture while continuously mixing the mixture at about 80 to 100° C. for a period of up to 60 minutes to form an emulsion, wherein the water forms up to 10% of the emulsion;
   leaving the emulsion to cool and macerate for between 1 and 12 hours
   sifting the emulsion to remove plant detritus,
wherein the composition is configured for being applied to skin and is formulated in a form selected from the group consisting of: a solid bar configured for being rubbed on skin, an ointment form, a cream form, an emulsion form, a lotion form, a suspension form, and a gel form.

2. The composition of claim 1, wherein the hydrogenated fats consist of at least one of soy wax and hydrogenated soy oil.

3. The composition of claim 1 wherein:
   the at least one plant extract from the first group forms about 0.1% to about 70% of the composition's weight; and
   each of all other plant extracts has a concentration between about 0.1% to about 10% of the composition's weight.

4. The composition of claim 1, wherein the final form of the composition is a fluid emulsion form and the composition is configured for being pumped through a pumping mechanism.

5. A method for improving one of peripheral circulation, lymph drainage, and treating at least one of varicose veins, swollen legs, painful legs, stasis dermatitis, swollen arms, indurated arms, hematomas, ecchymosis, periorbital dark circles, periorbital swelling, and hemorrhoids, the method comprising applying an effective amount of the composition of claim 1 to bare skin of a subject in need thereof.

6. A method for improving peripheral circulation and lymph drainage, and for treating at least one of varicose veins, swollen legs, painful legs, stasis dermatitis, swollen arms, indurated arms, hematomas, ecchymosis, periorbital dark circles, periorbital swelling, and hemorrhoids, the method comprising applying an effective amount of the composition of claim 2 to bare skin of a subject in need thereof.

7. A composition for improving peripheral circulation and lymph drainage, the composition comprising:
   (a) an effective amount at least one fat serving a base of the composition, selected from a first group consisting of the following fats: animal fat, palm oil, palm kernel oil (*Elaeis guineensis*), coconut oil (*Cocos nucifera*), cocoa butter (*Theobroma cacao*), shea butter (*Vitellaria paradoxa*), beeswax, and hydrogenated plant fat;
   (b) an effective amount of a first plant extract with astringent properties selected from a group of plant extracts consisting of: horse chestnut (*Aesculus hippocastanum*), vine leaves (*Vitis vinifera*), and *Galium verum;*
   (c) an effective amount of a second plant extract having a known desired effect on a biological system selected from the group consisting of: potato (*Solanum tuberosum*), lemon (*Citrus limon*), birch (*Betula pendula*), grapefruit seed (*Citrus paradisi*), and rice (*Oryza* spp);
   (d) an effective amount of an antioxidant component selected from the group consisting of dimethyl sulfoxide (DMSO) and allantoin forming up to 30% of the composition's weight and being present in at least a minimal amount required for the antioxidant component to exert direct biological actions as an antioxidant;
wherein the first and second plant extracts are extracted by maceration in the at least one fat, the maceration comprising: the maceration comprising:
   mixing plant parts with the at least one fat to generate a mixture;
   warming the mixture to about 80 to 100° C. while mixing;
   adding water to the mixture while continuously mixing the mixture at about 80 to 100° C. for a period of up to 60 minutes to form an emulsion, wherein the water forms up to 10% of the emulsion;
   leaving the emulsion to cool and macerate for between 1 and 12 hours
   sifting the emulsion to remove plant detritus,
wherein the composition is configured for being applied to skin and is formulated in a form selected from the group consisting of: a solid bar configured for being rubbed on skin, an ointment form, a cream form, an emulsion form, a lotion form, a suspension form, and a gel form.

8. A method for creating a composition that improves peripheral circulation and lymph drainage, the method comprising:
   (a) providing an effective amount at least one fat serving a base of the composition, selected from a group of fats consisting of the following fats: palm oil, palm kernel oil (*Elaeis guineensis*), coconut oil (*Cocos nucifera*), cocoa butter (*Theobroma cacao*), shea butter (*Vitellaria paradoxa*), beeswax, and hydrogenated plant fat;
   (b) providing an effective amount of an antioxidant component selected from a group consisting of dimethyl sulfoxide (DMSO) and allantoin forming up to 30% of the composition's weight and being present in at least a minimal amount required for the antioxidant component to exert direct biological actions as an antioxidant;

(c) extracting an effective amount of at least a first plant extract with astringent properties and an effective amount of at least a second plant extract having a known desired effect on a biological system via maceration with the at least one fat to generate a mixture, wherein:

(c1) the first plant extract is extracted from a first group of plants consisting of: horse chestnut (*Aesculus hippocastanum*), vine leaves (*Vitis vinifera*), and *Galium verum;*

(c2) the second plant extract is extracted from a second group of plants consisting of: potato (*Solanum tuberosum*), lemon (*Citrus limon*), birch (*Betula pendula*), grapefruit seed (*Citrus paradisi*), and rice (*Oryza* spp);

(c3) the maceration comprises:

(c3a) mixing plant parts and the antioxidant component with the at least one fat to generate a mixture;

(c3b) warming the mixture to about 80 to 100° C. while mixing;

(c3c) adding water to the mixture while continuously mixing the mixture at about 80 to 100° C. for a period of up to 60 minutes to form an emulsion, wherein the water forms up to 10% of the emulsion;

(c3d) leaving the emulsion to cool and macerate for between 1 and 12 hours;

(c3e) sifting the emulsion to remove plant detritus;

(c3f) leaving the emulsion to congeal to form the composition;

wherein the composition is formulated in a being selected from a group consisting of: a solid bar configured for being rubbed on skin, an ointment form, a cream form, an emulsion form, a lotion form, a suspension form, and a gel form;

wherein the composition is configured for being applied to skin.

9. The method of claim 8, wherein the hydrogenated plant fat extract at least one of comprises soy wax and hydrogenated soy oil.

10. The method of claim 8, comprising adding one or more additional plant extracts prior to the congealing of the emulsion, the one or more additional plant extracts comprising to one or more of:

at least one fat from the group of fats;

at least one extract extracted from at least one plant of the first group of plants;

at least one extract extracted from at least one plant of the second group of plants.

11. The method of claim 8 wherein plants may be whole, in parts, in powder form, fresh, or dry.

* * * * *